(12) United States Patent
Yu et al.

(10) Patent No.: US 9,393,277 B2
(45) Date of Patent: Jul. 19, 2016

(54) **APPLICATION OF *ALBIZZIA CHINENSIS* EXTRACT IN PREPARATION OF MEDICINE FOR TREATMENT OF GASTRIC ULCER**

(71) Applicant: Institute of Materia Medica, Chinese Academy of Medical Sciences, Beijing (CN)

(72) Inventors: Shishan Yu, Beijing (CN); Jianjun Zhang, Beijing (CN); Shuanggang Ma, Beijing (CN); Ruiming Xu, Beijing (CN); Chengxue Ji, Beijing (CN)

(73) Assignee: Institute of Materia Medica, Chinese Academy of Medical Sciences (CN)

( * ) Notice: Subject to any disclaimer, the term of this patent is extended or adjusted under 35 U.S.C. 154(b) by 0 days.

(21) Appl. No.: 14/353,926

(22) PCT Filed: Oct. 24, 2012

(86) PCT No.: PCT/CN2012/083458
§ 371 (c)(1),
(2) Date: Apr. 24, 2014

(87) PCT Pub. No.: WO2013/060275
PCT Pub. Date: May 2, 2013

(65) Prior Publication Data
US 2015/0010664 A1 Jan. 8, 2015

(30) Foreign Application Priority Data
Oct. 24, 2011 (CN) .......................... 2011 1 0326361

(51) Int. Cl.
*A61K 36/48* (2006.01)
(52) U.S. Cl.
CPC ..................................... *A61K 36/48* (2013.01)
(58) Field of Classification Search
None
See application file for complete search history.

(56) References Cited

FOREIGN PATENT DOCUMENTS

CN 101766676 A 7/2010

OTHER PUBLICATIONS

Perumal et al. (2010) Der Pharmacia Sinica, 1 (1): 95-103.*
Raskin et al. (2004) Current Pharmaceutical Design, 10, 3419-3429.*
Revilla et al. (1998) J. Agric. Food Chem. 46, 4592-4597.*
Liu et al., "Albizosides D and E, two new cytotoxic triterpene saponis from Albizia chinensis", Carbohydrate Research 345 (2010) 1877-1881.
Chinese Herbal Medicine editorial group, Second Edition, 1986, vol. 2, p. 768 (English summary provided).
International Search Report for Application No. PCT/CN2012/083458 dated Jan. 24, 2013.
Liu et al., "Cytotoxic Oleanane Triterpene Saponins from Albizia chinensis", J. Nat. Prod. 2009, 72, 632-639.
The dictionary of traditional Chinese Medicine, compiled by Jiangsu New Medical College, 1998, vol. 1, p. 937 (English summary provided).

* cited by examiner

*Primary Examiner* — Chris R Tate
*Assistant Examiner* — Russell Fiebig
(74) *Attorney, Agent, or Firm* — Lerner, David, Littenberg, Krumholtz & Mentlik, LLP

(57) ABSTRACT

The present invention discloses an *Albizzia chinensis* extract used in the preparation of a drug for the treatment of gastric ulcers. Specifically, it discloses an *Albizzia chinensis* (Osbeck) Merr extract and its preparation method including the stems bark of *Albizzia chinensis* was successively grounded, extracted, concentrated and purificated, as well as a pharmaceutical composition comprising the *Albizzia chinensis* extract. Through pharmacological test, it has been demonstrated that, the *Albizzia chinensis* extract showed strong inhibition activity against proton pumps, and it can be used for the treatment of gastric ulcers, chronic gastritis and other acid-related diseases, and its anti-ulcer effect is significant, quick, safe and reliable.

13 Claims, 2 Drawing Sheets

APPLICATION OF *ALBIZZIA CHINENSIS* EXTRACT IN PREPARATION OF MEDICINE FOR TREATMENT OF GASTRIC ULCER

CROSS REFERENCE TO RELATED APPLICATIONS

The present application is a national phase entry under 35 U.S.C. §371 of International Application No. PCT/CN2012/083458, filed Oct. 24, 2012, published in Chinese, which claims the benefit of Chinese Patent Application No. 201110326361.1, filed Oct. 24, 2011. The disclosures of said applications are incorporated by reference herein.

FIELD OF THE INVENTION

The present invention relates to medical field. Particularly it relates to an *Albizzia chinensis* (Osbeck) Merr. extract and the preparation method thereof, and it further relates to the use of an *Albizzia chinensis* extract in the preparation of a proton pump inhibitor and a drug for the treatment of gastric ulcer and acid related diseases.

BACKGROUND OF THE INVENTION

Gastric ulcer is a common disease of the digestive system, and easy to be recurred. With the stress of modern life, people are suffered from mental stress and work pressure, which led to the increasing incidence of gastric ulcers, and this disease endangers people's health. At present, some anti-ulcer drugs, such as ranitidine, omeprazole, and etc, are often clinically applied to the patient. Although the short-term efficacy of the chemical drugs is obvious, there are some side effects after taking those drugs. Therefore, people begin to research and develop new type of anti-ulcer drugs with high-efficiency and low toxicity. Based on long-term history of clinical practices, traditional Chinese medicine has been proved to have natural advantage and there is wide clinical application value for us to find and dig natural active ingredients or fractions from traditional Chinese herbal medicines for the treatment of gastric ulcer.

*Albizzia chinensis* (Osbeck) Merr. belongs to genus *Albizzia*, family Legume, and its medicinal part is mainly from the bark of the tree. Normally the bark contains tannin with the property of relieving diarrhea with astringents and promoting granulation and wound healing. It can be used for the treatment of enteritis, diarrhea, and dysentery. (The compilation of Chinese herbal medicine, compiled by the compilation of Chinese Herbal Medicine editorial group, Second Edition, 1986, volume 2, p 768). It was also reported that triterpene saponins (*Albizzia julibrissin* oxytocin) from the bark of *Albizzia chinensis* played a role in uterine contraction (The dictionary of traditional Chinese Medicine, compiled by Jiangsu New Medical College, 1998, volume 1, p 937). Recently, a series of complex triterpenoid saponins with cytotoxic activity isolated from of the bark of *Albizzia chinensis* have been published by the inventors (J. Nat. Prod. 2009, 72, 632-639; Carbohydr. Res. 2010, 345, 1877-1881). Moreover, we have also found that *Albizzia chinensis* extracts have sedative and hypnotic activity (China Patent Publication No. CN 101766676A). So far, there was no report about anti-gastric ulcer or anti-chronic gastritis pharmacology activity and proton pump inhibitory activity of the extract of the bark of *Albizzia chinensis*.

DETAILED DESCRIPTION OF THE INVENTION

The technical problem solved by the present invention is to provide a new class of drug, the *Albizzia chinensis* (Osbeck) Merr. extract, for the treatment of gastric ulcer and acid related diseases. The *Albizzia chinensis* (Osbeck) Merr. extract of the present invention can be used as a proton pump inhibitor to prepare a drug for treatment of gastric ulcer and acid-related diseases.

The second technical problem solved by the present invention is to provide a preparation method of an *Albizzia chinensis* (Osbeck) Merr. extract and the extract obtained by this method.

The third technical problem solved by the present invention is to provide a pharmaceutical composition, which comprises an *Albizzia chinensis* (Osbeck) Merr. extract acting as active component and pharmaceutically acceptable carrier.

The forth technical problem solved by the present invention is to provide the use of the *Albizzia chinensis* extract in the preparation of a drug for treatment of gastric ulcer and acid related diseases.

In order to solve the above technical problems, the present invention provides the following technical solutions:

The present invention relates to an *Albizzia chinensis* extract used for the preparation of a drug as a proton pump inhibitor for treatment of gastric ulcer and acid-related diseases, and the preparation method of the *Albizzia chinensis* extract is as follows:

(1) The raw material of *Albizzia chinensis* was crushed and extracted with a solvent, the solvent extract was concentrated to obtain a crude extract of *Albizzia chinensis*.

The preferred raw material of *Albizzia chinensis* is stem barks of *Albizzia chinensis*. The raw material of *Albizzia chinensis* is dried and properly smashed in order to increase the contact areas with solvents and to improve the efficiency of the extraction.

The solvents comprise alcohol or the mixture of water and alcohol. The preferred alcohols include methanol, ethanol, iso-propanol, butanol, etc.; the most preferred solvent is ethanol. The concentration of ethanol is 50-100% with the volume ratio of ethanol to $H_2O$, the preferred concentration is 80~95%.

The volume/weight (L/kg) ratio of extraction solvent to raw material is 3:1 to 10:1, the preferred volume/weight (L/kg) ratio of extraction solvent to raw material is 3:1 to 5:1.

The extraction can be carried out under static or dynamic conditions, preferably under dynamic conditions, such as under stirring condition. In order to improve the efficiency of the extraction, ultrasound extraction method can be used. The extraction is conducted at temperatures range from room temperature (eg 20° C.) to the solvent's reflux temperature, preferably under the temperature of reflux temperature. The extraction process can be continuous or intermittent, wherein the intermittent process can be repeated 1-5 times, preferably repeated 2-4 times. The extraction time ranges from 1 hour to 5 hours, preferably from 2 hours to 3 hours.

The solvent extracts were gathered, and concentrated by heating at atmospheric or reduced pressure to obtain an extractum, preferably concentrated under reduced pressure.

The preferred preparation method of *Albizzia chinensis* extractum is as follows: one kilogram of grounded barks of *Albizzia chinensis* is extracted with 3-5 liters of 80-95% EtOH in $H_2O$ under conditions of reflux for 2-4 times (each time, heated for 2-3 hours); and the solvent extracts are gathered, then the solvent was removed under reduced pressure to obtain *Albizzia chinensis* extractum.

(2) *Albizzia chinensis* extractum can be further purified by polyamide column chromatography, using alcohol solvent gradient to elute the extractum, and the *Albizzia chinensis* extract was obtained by refining and purifying.

The obtained *Albizzia chinensis* extractum was dissolved in 10-30% EtOH in $H_2O$, preferably in 20% EtOH in $H_2O$. The volume/weight (L/kg) ratio of polyamide adsorbent powder to *Albizzia chinensis* extractum is 20:1 to 40:1, the preferred ratio of polyamide powder to *Albizzia chinensis* extractum is 25:1 to 30:1.

The elution solvents comprise alcohol or the mixture of water and alcohol, the preferred alcohols include methanol and ethanol, and the most preferred solvent is ethanol. The ratio (V/V) of the elution solvent to polyamide powder is 3:1 to 10:1; the preferred ratio is 4:1 to 5:1. The gradient elution conditions are: 10-30% EtOH in $H_2O$, then 40-80% EtOH in $H_2O$. The 40-80% EtOH-eluted solution is concentrated to obtain an *Albizzia chinensis* extract.

The preferred purification steps comprise: the *Albizzia chinensis* extractum is dissolved in 10-30% EtOH in $H_2O$, and then subjected to column chromatography with 30-90 mesh polyamide column (the volume/weight (L/kg) ratio of polyamide adsorbent powder to *Albizzia chinensis* extractum is 25:1 to 30:1), successively eluting with 10-30% and 40-80% EtOH in $H_2O$, respectively, and the amount of elution solutions are 3-5 times of that of polyamide powder. The 40-80% EtOH-eluted solution is concentrated to obtain an *Albizzia chinensis* extract.

The present invention relates to a pharmaceutical composition, which comprises an *Albizzia chinensis* (Osbeck) Merr. extract prepared by the method described by the present invention and pharmaceutically acceptable carrier.

The present invention also relates to a pharmaceutical composition comprising the extract of the present invention as active component and commonly used drug excipients and/or additives. Normally, the pharmaceutical composition contains from 0.1 to 95 wt % of the extract of the present invention.

The present invention also provides a pharmaceutical composition comprising pharmaceutically effective amount of the *Albizzia chinensis* (Osbeck) Merr. extract of present invention as active ingredient and pharmaceutically acceptable carrier.

The pharmaceutical composition comprising *Albizzia chinensis* (Osbeck) Merr. extract of the present invention can be prepared according to the known method in the art. For this purpose, if necessary, any of the extract of the invention may be mixed with one or more commonly used drug excipients and/or additives in the form of solid or liquid. The composition may be formulated into the form for the treatment of human or as veterinary medicine.

The extract of the present invention or pharmaceutical composition thereof may be formulated into the unit dosage form. The extract can be administered by routes of enteral and/or parenteral methods, such as oral, intravenous, intramuscular, subcutaneous, intraperitoneal, nasal, oral mucosa, eyes, lungs, respiratory tract, skin, vagina, and/or rectum route. It is preferred to be orally administrated.

The dosage may be formulated in liquid form, solid form or semi-solid form. The liquid form may be solutions (including true solutions and colloidal solutions), emulsions (including o/w type, w/o type and complex emulsions), suspensions, injections (including aqueous injections, powder and infusion), eye drops, nose drops, lotions and/or liniments. The solid forms may be tablets (including ordinary tablets, enteric-coated tablets, buccal tablets, dispersible tablets, chewable tablets, effervescent tablets, orally disintegrating tablets), capsules (including hard capsules, soft capsules, enteric-coated capsules), granules, powders, pills, dripping pills, suppositories, films, patches, gas (powder) aerosols, sprays, etc. Semi-solid dosage may be in ointment form, gel form, paste form, etc.

The extract of the invention can be formulated into common formulation, sustained released formulation, controlled released formulation, target formulation or various microparticle systems.

For preparing solid compositions such as tablets, various excipients well known in the art may be employed. Excipients include diluents, binders, wetting agents, disintegrants, lubricants, glidants. The diluent may be starch, dextrin, sucrose, glucose, galactose, mannitol, sorbitol, xylitol, microcrystalline cellulose, calcium sulfate, calcium hydrogen phosphate, calcium carbonate, etc.; wetting agents may be water, ethanol, iso-propanol and the like; binders may be starch slurry, dextrin, syrup, honey, glucose solution, microcrystalline cellulose, gum arabic, gelatin, sodium carboxymethyl cellulose, methyl cellulose, hydroxypropyl methyl cellulose, ethyl cellulose, acrylic resin, carbomer, polyvinyl pyrrolidone pyrrole, polyethylene glycol and iso-propanol, etc.; disintegrating agent may be a dry starch, microcrystalline cellulose, low-substituted hydroxypropyl cellulose, crosslinked polyvinyl pyrrolidone, cross-linked sodium carboxymethyl cellulose, sodium carboxymethyl starch, sodium bicarbonate and citric acid, calcium carbonate, polyoxyethylene sorbitan fatty acid esters, dodecane sulfonate; lubricants and glidants may be talcum powder, silicon dioxide, stearic acid, tartaric acid, liquid paraffin, polyethylene glycol, etc.

The tablets of the present invention may be coated, such as sugar coating, film coating, enteric coating, or coated by two layers or multiple layers.

For preparing pills, various carriers well known in the art may be used. The examples of such carriers are diluents and absorbents, such as glucose, lactose, starch, cocoa butter, hydrogenated plant oil, polyvinylpyrrolidone, kaolin, talc; binders, such as gum acacia, gum tragacanth, gelatin, ethanol, honey, liquid sugar, rice paste or flour paste; disintergrating agent, such as agarose powder, dry starch, alginates, sodium dodecyl sulphate, methyl cellulose, ethyl cellulose, etc.

In order to prepare suppository, various carriers widely known in the art can be used, such as polyethylene glycol, lecithin, cocoa butter, higher alcohols, higher alcohol esters, gelatin, semi-synthetic glyceride, etc.

For preparing capsules, the extract of the present invention is mixed with the various carriers mentioned above, and the resulted mixture was encapsulated into hard or soft gelatin capsule. Also the extract of the present invention can be made into microcapsule, suspended in the aquatic medium as suspension, encapsulated into hard capsules or formulated into injections.

For example, the extract of the invention may be made as injectable formulations, such as solution, suspension, emulsion and froze-dried powder. Such formulation may be aqueous or non-aqueous, and may contain one and/or more pharmaceutically acceptable carrier, diluent, binder, lubricant, preservative, surfactant or dispersant. The diluent may be selected from water, ethanol, polyethylene glycol, 1,3-propanol, ethoxylated stearyl alcohol, polyoxided isostearyl alcohol, polyoxyethylene sorbitan fatty acid ester, etc. In addition, in order to prepare isotonic injections, proper amount of NaCl, glucose or glycerol can be added into the injectable formulations. Also routine cosolvent, buffer, pH-adjusting agent and the like can be added into the formulations. These additives are conventionally used in this field.

In addition, if necessary, colorants, preservatives, perfumes, flavoring agents, sweetening agents or other materials can be added into pharmaceutical formulations.

In order to achieve the purse of the mendicant to strengthen the performance of the treatment, the extract of the present invention of the pharmaceutical composition can be administrated by any known method in the art.

It is apparent to one skilled in the art that the therapeutically effective dose for active extracts of the invention or a pharmaceutical composition thereof will depend on various factors, such as the character and severity of the diseases to be treated, gender, age, weight, characteristic and individual response of the patients or animals, route and amount of the administration, and the treatment purpose. Therefore, the therapeutic dose according to the invention may vary greatly. In general, the dosages to be administrated may be readily determined by those skilled in the art. A therapeutically effective dose for use of the instant extract of the invention comprises a dose range of from about 0.001 to about 150 mg/kg weight/day, preferably from 0.1 to about 100 mg/kg weight/day, in particular from about 1 to about 60 mg/kg weight/day, more preferred from about 2 to about 50 mg/k weight g/day of active extracts. The total daily dosage may be administrated once or twice, three or four times a day. It will be understood, however, that the amount of the extracts actually administered will be determined by a physician according to his clinical experience and the other therapy protocol concurrently used. Every protocol may be administrated once or several times. The extract, its pharmaceutical composition of the present invention may be used independently or in combination with other therapeutic drugs with right dosage.

Studies on the effect of *Albizzia chinensis* extract of the present invention on hog gastric H+/K+-ATPase activity and pylorus ligation-induced ulcer in rats have proved that *Albizzia chinensis* extract has significant anti-gastric ulcer effect with the mechanism of the inhibition of H+/K+-ATPase activity.

Useful Technical Results

The present invention provides a new drug for the treatment of gastric ulcer and chronic gastritis. The preparation process of *Albizzia chinensis* extract is simple, and thus fits for industrializing production.

EMBODIMENTS

Figure 1:
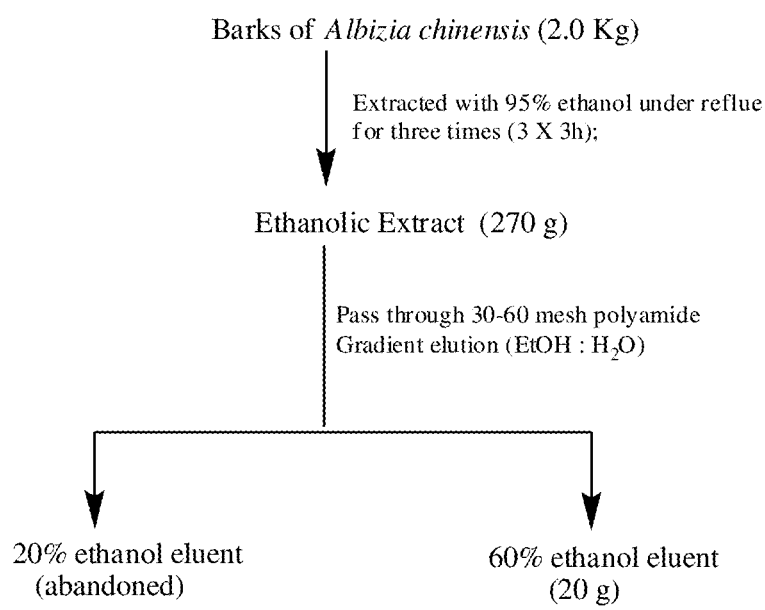
FIG. 1. Flowchart of the preparation of the *Albizzia chinensis* extract in Example 1.
Figure 2:
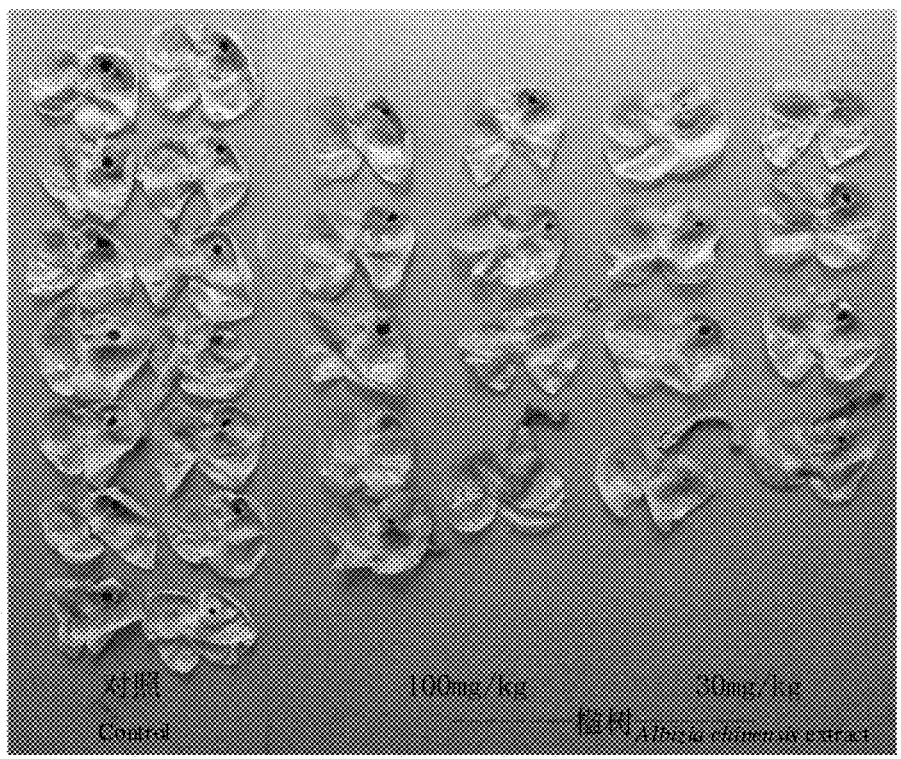
FIG. 2. Protective effect of *Albizzia chinensis* extract on acetic acid induced chronic gastric ulcer in rats.

The following examples are used to illustrate the present invention, with no means to limit the scope of the invention which can be understood by one skilled in the art.

Preparation Example

Example 1

Preparation of the *Albizzia chinensis* Extract

Air-dried and grounded barks of *Albizzia chinensis* (1 kg) were extracted with 3.5 liters of 95% EtOH under conditions of reflux for three times (each time, heated for three hours); and the liquid extract solution were gathered, then the solvent was removed under reduced pressure to give a extractum (130 g). The extractum was dissolved into 20% EtOH in $H_2O$, and then subjected to column chromatography with 30-60 mesh polyamide (powder, 3200 ml), successively eluting with 12 liters of 20% EtOH in $H_2O$ and 12 liters of 60% EtOH in $H_2O$. The 60% EtOH-eluted solution was concentrated to obtain an *Albizzia chinensis* extract (8.0 g).

Pharmacological Experiments

Example 1

*Albizzia chinensis* Extract Inhibits the Gastric $H^+/K^+$-ATPase Activity

Methods

Measurement of $H^+/K^+$-ATPase activity: A partially purified gastric mucosa of hog was incubated with *Albizzia chinensis* extract in buffer solution for 20 min at 37° C. ATP (20 mg/kg) was then added and the tubes were kept at 37° C. for 30 min. The reaction was stopped by adding 10% trichloroacetic acid and centrifuged at 6000 rpm for 10 min. The inorganic phosphate concentration of supernatant was determined using inorganic phosphorus reagent kit. The absorbance at 660 nm was read in a spectrophotometer. The $H^+/K^+$-ATPase activity was calculated.

Results

The result was listed in Tab. 1. The activity of $H^+/K^+$-ATPase was decreased by *Albizzia chinensis* extract (1 and 10 mg/l) by 28% and 73%, respectively. The extract showed potent inhibitory effect on hog gastric $H^+/K^+$-ATPase activity.

TABLE 1

| Effect of *Albizzia chinensis* extract on hog gastric $H^+/K^+$-ATPase activity | |
|---|---|
| Concentration (mg/L) | Inhibitory rate (%) |
| 1 | 28 |
| 10 | 73 |

Example 2

*Albizzia chinensis* extract has gastro-protective effect on pylorus ligated gastric ulcer in rats.

Methods

Male rats were used after 48 h of fasting and randomly divided into three groups. Physiological saline and *Albizzia chinensis* extract (100 and 500 mg/kg) were administered intraduodenally immediately after pylorus ligation. Pylorus ligation was performed under light anesthesia with diethylether. The animals were sacrificed at 20 h after ligation. The stomachs were removed and opened to determine the lesion. The results were analyzed using One-way ANOVA to determine the significance test.

Results

The result was listed in Tab. 2. Gastric ulcer inhibition was found to be 43% and 86% (p<0.05) at the doses of 100 and 500 mg/kg, respectively. It therefore suggests that *Albizzia chinensis* extract significantly decreased the occurrence of the gastric ulcer.

TABLE 2

Effect of *Albizzia chinensis* extract
on pylorus ligation-induced ulcer in rats

| Dose (mg/kg, ig) | Reduction of gastric ulcer (%) |
|---|---|
| 100 | 43 |
| 500 | 86 |

Example 3

*Albizzia chinensis* extract has gastro-protective effect on acetic acid induced chronic gastric ulcer in rats.

Methods

Rats were used after 48 h of fasting. After anesthesia with pentobarbital sodium, 30% (v/v) acetic acid (20 μl) was injected into subserosal layer in the glandular part of pylorus. The animals were randomly divided into three groups and treated with *Albizzia chinensis* extract (30 and 100 mg/kg, ig) once daily for 10 days after induction of gastric ulcer. The animals were sacrificed; stomachs were removed and opened, spread on the glass plate. The pictures were taken with digital camera and the area ($mm^2$) of ulceration was determined using Spot Advanced software.

Results

The result was listed in Tab. 3. Gastric ulcer inhibition was found to be 57% and 50% ($p<0.01$) at the doses of 30 and 100 mg/kg, respectively. The result showed that *Albizzia chinensis* extract significantly decreased the acetic acid induced chronic gastric ulcer in rats.

TABLE 3

Effect of *Albizzia chinensis* extract on acetic
acid induced chronic gastric ulcer in rats

| Group | Dose (mg/kg, ig) | Area of ulceration ($mm^2$) | Reduction of gastric ulcer (%) |
|---|---|---|---|
| Model | | 17.4 ± 4.4 | |
| *Albizzia chinensis* extract | 100 | 8.8 ± 7.0 ** | 49.7 |
| | 30 | 7.5 ± 6.0 *** | 57.2 |

The area of ulceration was expressed as mean ± SEM.
** $p < 0.01$,
*** $p < 0.001$ vs. model group.

The invention claimed is:

1. A method of treating gastric ulcers or chronic gastritis in a patient in need thereof comprising administering a therapeutically effective amount of *Albizzia chinensis* extract to said patient, wherein the *Albizzia chinensis* extract is prepared by a method comprising the steps of:
    (A) extracting ground bark of *Albizzia chinensis* with 80-95% ethanol extraction solvent under conditions of reflux with heating for 2-3 hours and removing the ethanol extraction solvent under reduced pressure to obtain a crude extract,
    (B) dissolving the crude extract in 10-30% ethanol solution to obtain a dissolved mixture,
    (C) applying the dissolved mixture to a 30-90 mesh polyamide chromatograph column, wherein the volume: weight ratio of polyamide to crude extract is 25:1 to 30:1,
    (D) passing a first elution solution of 10-30% ethanol through the chromatograph column,
    (E) passing a second elution solution of 40-80% ethanol through the chromatograph column to obtain an extractum solution, and
    (F) concentrating the extractum solution to obtain said *Albizzia chinensis* extract.

2. The method of claim 1, wherein in the extracting step A said solvent further comprises water.

3. The method of claim 1, wherein the extracting of the ground bark with ethanol under conditions of reflux is performed 2-4 times and the solvent extracts are combined and the solvent is removed under pressure to produce the crude extract.

4. The method of claim 1, wherein the volume of the first and/or second elution solution is 3-5 times the amount of the polyamide.

5. The method of claim 1, wherein the *Albizzia chinensis* extract is administered enterally.

6. The method of claim 1, wherein the *Albizzia chinensis* extract is administered orally.

7. The method of claim 6, wherein the *Albizzia chinensis* extract is formulated in a solid or liquid dosage form.

8. The method of claim 1, wherein the *Albizzia chinensis* extract is administered parenterally.

9. The method of claim 1, wherein the *Albizzia chinensis* extract is administered via injection.

10. The method of claim 1, wherein the therapeutically effective amount is from about 1 to about 60 mg/kg of body weight per day.

11. The method of claim 1, wherein the therapeutically effective amount is from about 2 to about 50 mg/kg of body weight per day.

12. The method of claim 1, wherein the patient is human.

13. The method of claim 1, wherein the patient is an animal.

* * * * *